United States Patent [19]

Leviton

[11] 4,384,580

[45] May 24, 1983

[54] SUCTION CANISTER SYSTEM AND ADAPTER FOR SERIAL COLLECTION OF FLUIDS

[75] Inventor: Jan Leviton, East Brunswick, N.J.

[73] Assignee: Becton, Dickinson and Company, Paramus, N.J.

[21] Appl. No.: 287,841

[22] Filed: Jul. 29, 1981

[51] Int. Cl.³ .............................................. A61M 1/00
[52] U.S. Cl. ..................................... 604/119; 141/35; 604/323; 604/319
[58] Field of Search ................ 128/276, 760; 137/205; 141/35, 36, 59, 202, 286; 119/14.06, 14.46

[56] References Cited

U.S. PATENT DOCUMENTS

| | | | |
|---|---|---|---|
| 1,962,192 | 6/1934 | Hapgood | 119/14.06 |
| 3,719,197 | 3/1973 | Pannier, Jr. et al. | 128/276 |
| 3,863,664 | 2/1975 | Holbrook et al. | 137/205 |
| 4,111,204 | 9/1978 | Hessel | 128/276 |

FOREIGN PATENT DOCUMENTS

| | | | |
|---|---|---|---|
| 512631 | 5/1955 | Canada | 119/14.46 |
| 672582 | 10/1963 | Canada | 119/14.06 |

OTHER PUBLICATIONS

Catalog Cut "CRD System" Medi-Vac Corp., Abilene, Texas 79604.

Primary Examiner—Richard J. Apley
Assistant Examiner—J. L. Kruter
Attorney, Agent, or Firm—Richard J. Rodrick

[57] ABSTRACT

A suction canister system for serial collection of fluids comprises a plurality of canisters. Vacuum is provided to the interior of the canisters each of which includes a valve for terminating the vacuum in the canister responsive to the level of fluid therein. The fluid is allowed to travel to a serially arranged canister when the valve on one canister is closed.

A fluid flow adapter suitable for use in a fluid collection container includes a first open tube with second and third open tubes attached thereto. The second and third tubes are in direct fluid communication with the first tube but they are not in direct fluid communication with each other. This arrangement allows the second and third tubes to serve as fluid inlet and fluid outlet openings for the collection container.

7 Claims, 5 Drawing Figures

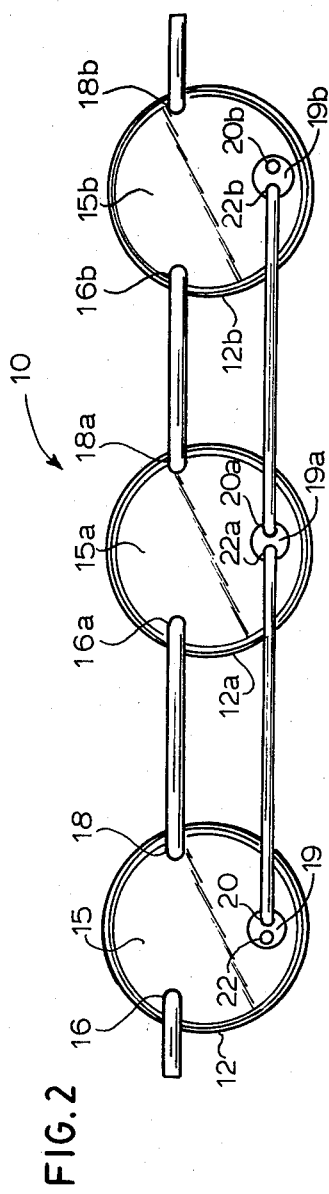

SUCTION CANISTER SYSTEM AND ADAPTER FOR SERIAL COLLECTION OF FLUIDS

BACKGROUND OF THE INVENTION

1. Field of the Invention

The present invention relates to a suction canister system useful in the collection of fluids such as from a patient during a surgical procedure, and also concerns an adapter suitable for use in a suction canister to assist in providing a system through which fluids can be collected serially.

2. Description of the Prior Art

Suction canisters are employed in the hospital environment, and particularly during surgical procedures, to drain body fluids from a patient. In general, suction canisters employ a collection system and a vacuum source, such as a pump, to facilitate this drainage procedure. Each canister generally includes a flexible line or hose connected to the vacuum source so that vacuum can be applied to the interior of the canister. Another flexible line or hose extends from the canister to the source of body fluids in the patient. Once the vacuum is applied, a negative pressure gradient is communicated through the interior of the suction canister so that body fluids are drawn into the canister.

In many procedures the volume of fluid to be collected exceeds the capacity of a single suction canister used for these purposes. It is, therefore, desirable to be able to collect fluids continuously from the patient without the need to terminate the suction operation. To this end, a serial collection arrangement has been sought whereby a number of suction canisters are connected in fluid communication with each other and when the first suction canister has been filled the fluid travels through appropriate tubing and starts filling the second canister, and so forth. This serial collection arrangement provides an additional benefit in that the single filling procedure might leave some of the canisters unused whereby they can be preserved for further use. One such serial flow suction canister system is described in U.S. Pat. No. 3,863,664.

While the serial flow system of the aforementioned patent is workable and practicable, the advent of improved suction canisters has caused some problems to arise when connecting suction canisters in a serial flow arrangement. In particular, many suction canisters now employ a valve inside the canister, associated with the vacuum port, and typically responsive to the height of fluid in the canister to terminate suction coming in. In order to provide a serial flow connection to a plurality of canisters, the clinicians oftentimes have been instructed to remove the valve in all of the canisters except the last one in the serial flow arrangement. Not only are special instructions involved with this type of manipulation, but the unused valves are normally discarded representing an expenditure for product not being utilized. To further complicate the situation, many suction canisters are now provided with a flexible collection bag inside the canister. When valves are used in suction canisters also employing a flexible collection bag, it is awkward and cumbersome for the clinician to try to remove the valve from the vacuum port. This is due to the fact that the flexible bag is typically sealed to the canister cover completely surrounding the valve. Thus, the clinician has to feel for the valve through the flexible bag and, when removed, the valve would drop into the bag itself to thereby free the vacuum port for fluid flow therethrough in the serial flow arrangement. Such a suction canister with flexible bag and valve is described in U.S. Pat. No. 4,111,204.

Inasmuch as the more recent suction canisters with valves or flexible bags are more difficult to arrange in a serial flow collection combination, improvements are still being sought to facilitate such an arrangement for use in the serial collection of fluids, particularly from patients in the hospital environment. It is to such an improvement that the present invention is directed.

SUMMARY OF THE INVENTION

A first aspect of the present invention includes a suction canister system for serial collection of fluids comprising a plurality of canisters. Means is included for providing vacuum to the interior of the canisters including valve means for terminating the vacuum in each canister responsive to the level of fluid therein. Fluid is allowed to travel to a serially arranged canister when the valve on one cylinder is closed. In one embodiment of this aspect of the invention, the vacuum providing means includes a plurality of suction lines interconnecting adjacent canisters. At least one of the lines between adjacent canisters is adapted to prevent fluid from traveling from one canister to the serially arranged adjacent canister.

Another aspect of the present invention is a fluid flow adapter suitable for use in a fluid collection container, such as a suction canister. This adapter comprises a first open tube, with second and third open tubes attached to the first tube. Both the second and third tubes are in direct fluid communication with the first tube but are not in direct fluid communication with each other. Preferably, the second and third tubes include means for closing the same to prevent the flow of fluid therethrough. The second and third tubes serve as fluid inlet and fluid outlet ports to the fluid collection container during use.

In accordance with the principles of the present invention, a suction canister system allows the serial collection of fluids into the individual canisters. The independency of fluid collection contemplated by the present invention allows convenient canister connection in the fluid collection arrangement for as many canisters as might be required for the operation at hand. In the same fashion, removal of an unused canister is simplified. While the suction canister system of the present invention may provide a serial fluid flow arrangement in canisters without valve controls, it is particularly adapted to be employed in suction canisters normally including a valve associated with the vacuum port. Furthermore, the present suction canister system is adapted to provide a serial fluid flow engagement for canisters which include a flexible bag therein for the collection of fluids. In the flexible bag suction canisters, there is normally a separation of vacuum applied to the interior of the canister so that vacuum is applied to the interior of the bag as well as to the space inside of the canister but exterior to the bag. The present invention provides a readily assembled system for the serial fluid flow arrangement without disturbing the separation of vacuum feature which flexible bag suction canisters utilize. An overall advantage is the ease with which the suction canister is assembled to provide serial flow of fluid therethrough. The suction lines connect the various canisters in a fashion easily understood by the operator.

BRIEF DESCRIPTION OF THE DRAWINGS

FIG. 1 is a side elevational view of one embodiment of the present invention illustrating a suction canister system including canisters with valves for vacuum control;

FIG. 2 is a top plan view of the suction canister system of FIG. 1;

DETAILED DESCRIPTION

Figure 3:
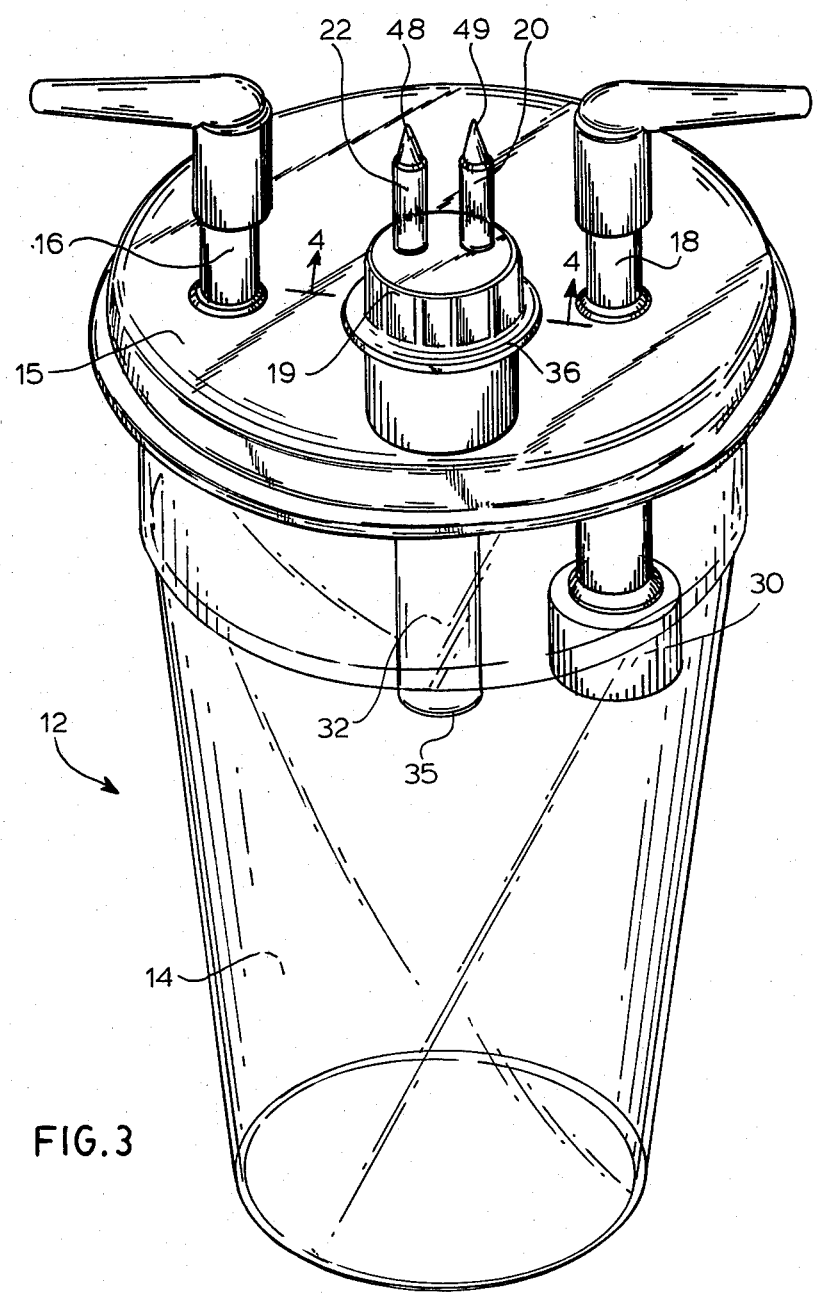
FIG. 3 is an enlarged perspective view illustrating one suction canister of the suction canister system of FIG. 1.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

Adverting now to the drawings and FIGS. 1-3 in particular, there is illustrated a suction canister system 10 as it may appear utilizing the principles of the present invention and including three canisters 12, 12a and 12b, respectively. (The suffixes "a" and "b" will be used hereinafter to designate similar elements on successively arranged canisters in suction canister system 10.) While the drawings herein illustrate three such suction canisters for purposes of describing exemplary embodiments of the present invention, it is understood that for serial collection of fluids at least two such canisters are needed with there being no limit on the maximum number, except for practical reasons. Also, while it is typical that a suction canister system for serial collection of fluids will employ similar canisters throughout the system, such as illustrated in FIGS. 1 and 2, it is understood that there may be a mix of different canisters in any particular system. For example some canisters may include flexible bags or valves for vacuum control, whereas other canisters may not include these elements. In the embodiment of FIGS. 1-3, each canister includes a receptacle 14 for the collection of fluids therein. Typically, the receptacles are clear, rigid plastic holding anywhere from about 1,000-3,000 cubic centimeters of fluid. Each receptacle 14 is normally cup-shaped with an open top. The top is sealed preferably with a removable cover 15. Plastic is usually employed in the fabrication of cover 15. In the embodiment of FIGS. 1-3, cover 15 includes two vacuum ports 16 and 18, respectively, and an adapter 19 which is preferably removable from cover 15 and includes a fluid inlet port 20 and a fluid outlet port 22 to be described more completely hereinafter. All of the aforementioned ports communicate with the interior of receptacle 14.

A length of preferably flexible tubing 24 interconnects vacuum port 18 on canister 12 with vacuum port 16a on canister 12a; a length of preferably flexible tubing 24a similarly interconnects canisters 12a and 12b. Another length of tubing 25 is connected to vacuum port 16 on canister 12 which is intended to serve as the last of the canisters in the serial arrangement for collection of fluids. Tubing 25 includes an end 26 adapted to be connected to a source of vacuum (not shown). At the opposite end of suction canister system 10, on the first canister 12b in the serial line for collection of fluids, another length of tubing 28 is connected to vacuum port 18b. Tubing 28 has an open end 29 adapted to be connected to a source of fluid outside of the canister system, such as, for example, in the body of a patient from whom fluids are to be collected.

Each of canisters 12, 12a and 12b in the embodiment being described includes a valve 30 on the interior side of vacuum port 16, 16a and 16b, respectively. The purpose of valve 30 is to terminate suction through port 16 when the level of fluid in canister 14 rises to a predetermined level. There are a variety of such valves utilized on suction canisters which are well known in the art. One such valve is a float valve which seals off port 16 by floating against a valve seat associated therewith (not shown) in response to the rising level of fluid in the canister. It is this valve which the operator would have to remove, but for the features of the present invention, in order to provide a serial flow arrangement. As thus described, before pointing out the details of adapter 19, the canister system is similar to the serial flow arrangement described in U.S. Pat. No. 3,863,664. Therefore, if tubing 25 were to be connected to a source of vacuum, suction would be pulled successively through each of the three canisters in a serial flow path. Particularly, suction would be drawn through tubing 28 and out of canister 12b through tubing 24a, into canister 12a, then out of canister 12a through tubing 24 and into canister 12, then out of tubing 25 toward the vacuum source. If tubing 28 is positioned in a source of fluid, the vacuum conditions would draw the fluid therethrough into receptacle 14b. Fluid rising therein would then contact valve 30b shutting down the vacuum through tubing 24a. Therefore, no fluid would be permitted to travel from canister 12b to 12a with valve 30b operatively maintained. Therefore, adapter 19 has been provided through a third opening in cover 15 in order to effectively by-pass the valve in the various canisters.

Figure 4:
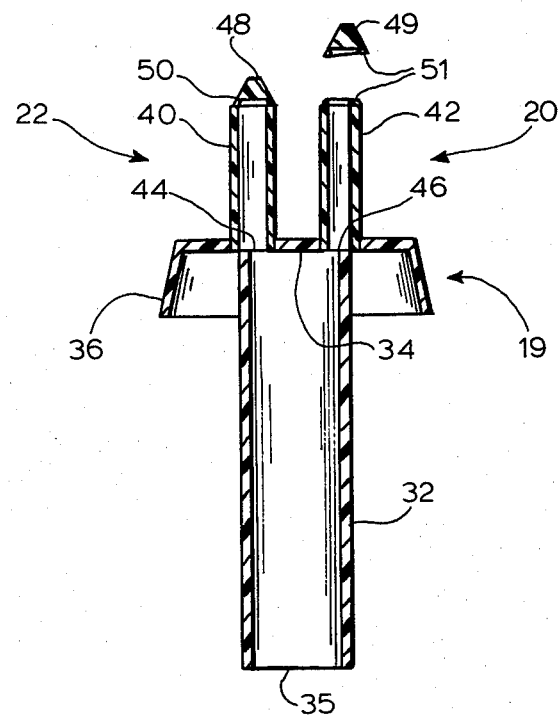
FIG. 4 is a cross-sectional view of the adapter of FIG. 1 taken along line 4—4 thereof.

Specifically, and referring to FIG. 4 in conjunction with FIGS. 1-3, adapter 19 includes a first, hollow tube 32 having open ends 34 and 35, respectively. A cap 36 is attached over open end 34 and serves as a connective lid to be attached to the opening 38 through cover 15. It is preferred that lid 36 be removable from cover 15 so that opening 38 can also serve as a pour spout for decanting fluids from the canister. When lid 36 is attached to cover 15 through opening 38, tube 32 will depend downwardly into receptacle 14. To this end, it is preferred that tubing 32 be long enough so that open distal end 35 is positioned at a level in the receptacle lower than float valve 30. This will assure that fluid rising inside the receptacle is drawn into tubing 32 before rising fluid engages the float valve. Attached to the other side of lid 36 are two preferably smaller hollow tubes 40 and 42. It is also preferred that tubes 40 and 42, as well as tube 32 be positioned substantially parallel to each other. Furthermore, there are openings 44 and 46 through lid 36 so that each of tubes 40 and 42, respectively, are in fluid communication with tube 32. It is noted, however, that each of tubes 40 and 42 are not in direct fluid communication with each other. To assure adequate fluid flow through the respective tubes, it is also preferred that tube 32 have a larger diameter than the individual diameters of tubes 40 and 42. Since tube 32 preferably extends a substantial distance into receptacle 14, it is preferred that tube 32 be longer than tubes 40 and 42.

Each of tubes 40 and 42 is preferably formed of a material, such as plastic, which would permit the integral formation of caps 48 and 49 at the ends of the respective tubes. A weakened area 50 and 51 is desirably formed between the cap segments and the main body of the tubes. This will allow the user to twist or break the caps from the tubes, preferably at the same time the suction canister system is being assembled. In FIG. 4, cap 49 is illustrated as being separated from tube 42 due to the frangible nature of the original connection. Thus, during use, either one or both of the respective caps can be removed for the required fluid inlet or outlet connections as may be desired. It is, of course, understood that the caps need not be originally integrally formed on tubes 40 and 42; other caps, such as snap-on caps, plugs and the like can also be employed within the purview of this invention to seal off the open ends of the tubes. As described above, tubing 40 and opening 44 represent fluid outlet opening 22, while tubing 42 and opening 46 represent fluid inlet opening 20. It is appreciated that either tube could be used for the fluid inlet or outlet to be described hereinafter.

Referring now particularly to FIGS. 1 and 2, fluid inlet port 20 on canister 12 is connected by tubing 54 to fluid outlet port 22a on canister 12a. Similarly, fluid inlet port 20a is connected by tubing 54a to fluid outlet port 22b on canister 12b. It is noted that there are no tubing connections made to port 22 on canister 12 or port 20b on canister 12b. On those ports where there are no tubing connections, the ends of the ports remain sealed, such as with caps 48 or 49. On the other hand, on those ports where tubing interconnections are to be made, the caps are removed from the ports so that fluid can flow therethrough.

In operation, such as with the vacuum conditions as described above, tubing 28 is connected to the source of fluid. Under the negative pressure conditions caused by the vacuum through the suction canister system, fluid enters receptacle 14b and starts filling same. When the level reaches opening 35b of adapter 19b, fluid then flows through tubing 54a and through adapter 19a whereupon the fluid is deposited in receptacle 14a. It is noted that this path of fluid by-passes valve 30b and tubing 24a during the serial collection of fluid. In this fashion, each of the canisters in the present suction canister system can be filled in succession without the need to remove the valves before the collection procedure begins.

It should also be noted that whereas tubing 28 is connected to port 18b for inlet of fluids into canister 12b, this tubing could also be connected to inlet port 20b. However, since inlet port 20b normally includes a cap therefor, it is preferable to connect tubing 28 to the existing port 18b; otherwise, port 18b would have to be stoppered in order to preserve the vacuum integrity of the system.

Figure 5:
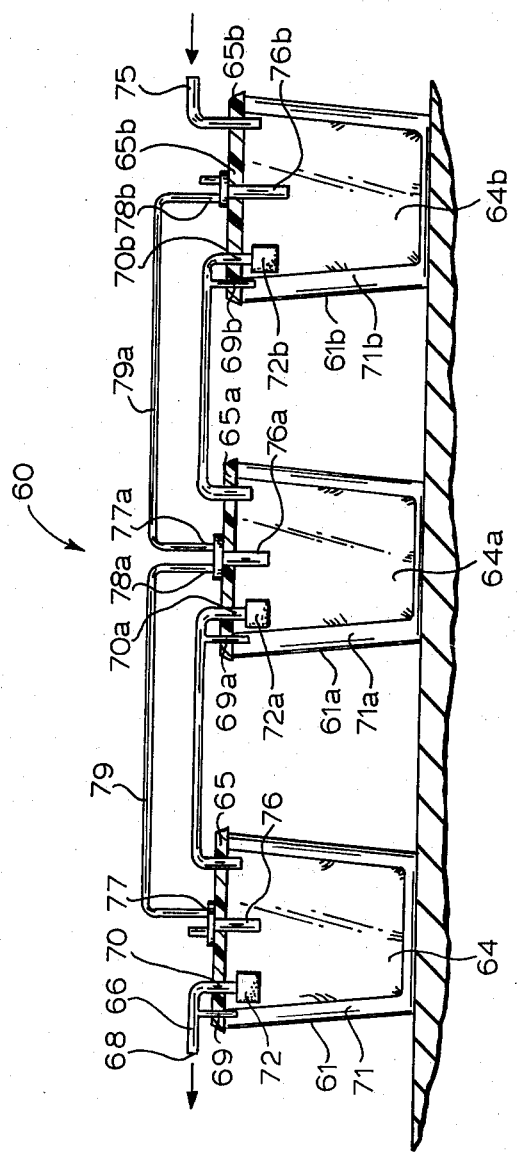
FIG. 5 is a side elevational view of another embodiment of the canister system of the present invention with each canister including a flexible fluid collection bag and a valve for fluid control.

Referring now to FIG. 5, suction canister system 60 is illustrated including canisters 61, 61a and 61b. Inside receptacle 62 is a flexible collection bag 64 sealed to cover 65 and depending into the receptacle. Cover 65 has ports therethrough similar to the previously described embodiment, including the tubing interconnections between adjacent canisters. However, the tubing connection through cover 65 for pulling suction out of the canisters has been somewhat modified. Tubing 66 includes an open end 68 which is adapted to be connected to a source of vacuum. Tubing 66 is connected to two vacuum ports 69 and 70 extending through cover 65. Vacuum port 69 is in fluid communication with the interior of receptacle 71 in the space exterior to collection bag 64. On the other hand, vacuum port 70 is in fluid communication with the interior of collection bag 64. A valve 72 is provided on the interior side of vacuum port 70 for the same purposes as in the previous embodiment.

The embodiment of FIG. 5 is operated by connecting tubing 66 to a source of vacuum. On the other end of the system, tubing 75 is placed in a source of fluid, for example, in the body of a patient during a surgical procedure. Negative pressure caused by the vacuum conditions in the canisters draws fluid through tubing 75 into flexible bag 64b. The suction applied to the space exterior to the collection bag through vacuum port 69b contributes to keeping flexible bag 64b open during the fluid collection procedure. When fluid inside bag 64b rises to the level of valve 72b, the valve terminates suction through vacuum port 70b. On the other hand, rising fluid enters tube 76b and passes through fluid outlet port 78b. Fluid travels through tubing 79a and fluid inlet port 77a in canister 61a. While fluid is thus being serially delivered from one canister into the next adjacent canister, suction remains applied through ports 69a and 70a. This procedure continues until the last canister is filled. In the embodiment being described, when fluid inside flexible bag 64 in canister 61 rises to the level of valve 72, all suction forces to the interior of the collection bags are terminated automatically due to the valving arrangement with respect to vacuum port 70.

Thus, the present invention provides a suction canister system for serial collection of fluids particularly useful with suction canisters including fluid control valves or fluid collection bags therein. Furthermore, the present invention provides a suitable adapter for allowing the tubing interconnections between adjacent canisters in the serial flow arrangement.

What is claimed is:

1. A suction canister system for serial collection of fluids comprising:
a plurality of canisters, each canister including: a receptacle and a cover having two vacuum ports communicating with the interior of the receptacle except for the first canister in the serial line for collection of fluids wherein there is only one vacuum port, means including a fluid inlet port for the flow of fluid therethrough into the receptacle, and means including a fluid outlet port for the flow of fluid therethrough out of the receptacle except for the last canister in the serial line for collection of fluids wherein there is no fluid outlet port; and
means including a vacuum port in the canister last in the serial line for collection of fluids for connections to a source of vacuum, a vacuum port of one canister connected to a vacuum port on a successive canister in a serial flow arrangement whereby vacuum is applied through a canister before reaching an adjacent canister, a vacuum port in each cover including a valve on the interior side thereof inside the receptacle for preventing fluid from flowing out of the receptacle through the associated vacuum port, the inlet port on the canister first in the serial line for collection of fluids including means for connection to a source of fluid outside of the canister system, and the outlet port on each canister connected to the inlet port on a successive canister in a serial fluid flow arrangement for the collection of fluid in said canisters successively, each canister further including a removable adapter for making the outer port-inlet connections, wherein said adapter includes a cap means to fit onto an opening through the canister cover, a downwardly extending open tube and two upwardly extending open tubes each in fluid communication with the downwardly extending tube, one of said upwardly extending tubes serving as a fluid inlet port, the other of said upwardly extending tubes serving as a fluid outlet port in the canisters having such fluid inlet and fluid outlet ports.

2. The canister system of claim 1 wherein said valve in each canister is a float valve adapted to terminate suction therethrough responsive to the rising level of fluid in the receptacle.

3. A suction canister system for serial collection of fluids comprising:

a plurality of canisters, each canister including: a receptacle and a cover having two vacuum ports communicating with the interior of the receptacle except for the first canister in the serial line for collection of fluids wherein there is only one vacuum port, means including a fluid inlet port for the flow of fluid therethrough into the receptacle, and means including a fluid outlet port for the flow of fluid therethrough out of the receptacle except for the last canister in the serial line for collection of fluids wherein there is no fluid outlet port; and means including a vacuum port on the canister last in the serial line for collection of fluids to a source of vacuum, a vacuum port of one canister connected to a vacuum port on a successive canister in a serial flow arrangement whereby vacuum is applied through a canister before reaching an adjacent canister, a vacuum port in each cover including a float valve on the interior side thereof inside the receptacle responsive to the rising level of fluids in the receptacle for preventing fluid from flowing out of the receptacle through the associated vacuum port, the inlet port on the canister first in the serial line for collection of fluids including means for connection to a source of fluids outside of the canister system, and the outlet port on each canister connected to the inlet port on a successive canister in a serial fluid flow arrangement for the collection of fluid in said canisters successively, each canister including an extension tube extending downwardly from said fluid outlet port into said receptacle, said tube having an open distal end positioned inside said receptacle at a level therein lower than said valve so that fluid rising inside said receptacle is drawn into said tube before rising fluid engages said valve.

4. The canister system of claims 2 or 1 wherein each canister includes a flexible collection bag positioned in the receptacle and means for providing vacuum to the interior of said collection bag and to the space inside said receptacle exterior to said collection bag.

5. The canister system of claim 4 wherein a vacuum port of each canister communicates with said space exterior to said collection bag for providing vacuum thereto.

6. The canister system of claim 5 wherein the vacuum port of each canister which communicates with said exterior space also communicates with the interior of said collection bag.

7. The canister system of claim 1 wherein the adapter in the first and last canisters in the serial collection arrangement has one of said upwardly extending tubes closed whereby in said first collection canister the upwardly extending tube which is open serves as a fluid outlet port and in said last collection canister the upwardly extending tube which is open serves as a fluid inlet port.

* * * * *